(12) United States Patent
Mimura et al.

(10) Patent No.: US 8,871,942 B2
(45) Date of Patent: Oct. 28, 2014

(54) PROCESS FOR PRODUCING 1-TRIAZOLE-2-BUTANOL DERIVATIVES

(75) Inventors: Mitsuo Mimura, Fujieda (JP); Masahito Watanabe, Fujieda (JP); Nobuo Ishiyama, Kyoto (JP); Takuya Yamada, Kyoto (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/818,897

(22) PCT Filed: Aug. 31, 2011

(86) PCT No.: PCT/JP2011/069733
§ 371 (c)(1),
(2), (4) Date: Feb. 25, 2013

(87) PCT Pub. No.: WO2012/029836
PCT Pub. Date: Mar. 8, 2012

(65) Prior Publication Data
US 2013/0150586 A1    Jun. 13, 2013

(30) Foreign Application Priority Data
Aug. 31, 2010   (JP) .................. 2010-194068

(51) Int. Cl.
*C07D 401/06*   (2006.01)

(52) U.S. Cl.
CPC .................... *C07D 401/06* (2013.01)
USPC ........................................................ 546/210

(58) Field of Classification Search
None
See application file for complete search history.

(56) References Cited

U.S. PATENT DOCUMENTS 6,054,586 A    4/2000   Naito et al.

FOREIGN PATENT DOCUMENTS

| EP | 0698606 | 2/1996 |
|---|---|---|
| WO | 9426734 | 11/1994 |
| WO | 9711939 | 4/1997 |

OTHER PUBLICATIONS

Bergman, 25(4) J. Phys. Chem. Ref. Data (1996).*
Serajuddin et al., 59 Adv. Drug Del. Rev. 603-616 (2007).*
Mimura et al., "Synthesis and Evaluation of (Piperidinomethylene)bis(phosphonic acid) derivatives as Anti-osteoporosis Agents", Chem. Pharm. Bull., 41(11):1971-1986 (1993).
Ogura et al., "Synthesis and Antifungal activities of (2R,3R)-2-Aryl-1-azolyl-3-(substituted amino)-2-butanol dreivatives and topical antifungal agents", Chem. Pharm. Bull., 47(10):1417-1425 (1999).
Chakraborti et al., "Lithium Bromide, an Inexpensive and efficient catalyst for opening of epoxide rings by amines at room temperature under solvent-free condition", Eur. J. Org. Chem., 17:3597-3600 (2004).
International Preliminary Report on Patentability for PCT/JP2011/069733 dated Mar. 12, 2013, with Written Opinion.
Shivani et al., "Zinc(II) Perchlorate Hexahydrate Catalyzed Opening of Epoxide Ring by Amines: Applications to Synthesis of (RS)/(R)-Propranolols and (RS)/(R)/(S)-Naftopidils", J. Org. Chem., 72:3713-3722 (2007).
Heydari et al., "A New and efficient epoxide ring opening via poor nucleophiles: indole, p-nitroaniline, borane and O-Trimethylsilylhydroxylamine in lithium perchlorate", Synthesis, 10:1563-1565 (2004).

* cited by examiner

*Primary Examiner* — Janet L Andres
*Assistant Examiner* — Timothy R Rozof
(74) *Attorney, Agent, or Firm* — Sughrue Mion, PLLC

(57) ABSTRACT

An object is to provide a process for producing the compound of formula 1 in higher yield by the ring-opening addition reaction of epoxytriazole with amine under mild conditions without using a large excess of 4-methylenepiperidine. The process for producing (2R,3R)-2-(2,4-difluorophenyl)-3-(4-methylenepiperidin-1-yl)-1-(1H-1,2,4-triazol-1-yl)butan-2-ol or an acid addition salt thereof comprises reacting (2R,3S)-2-(2,4-difluorophenyl)-3-methyl-2-[(1H-1,2,4-triazol-1-yl)methyl]oxirane with an acid addition salt of 4-methylenepiperidine in a reaction solvent in the presence of a hydroxide of an alkali metal or an alkaline earth metal selected from the group consisting of lithium, sodium, calcium, and strontium, or a hydrate thereof.

7 Claims, No Drawings

PROCESS FOR PRODUCING 1-TRIAZOLE-2-BUTANOL DERIVATIVES

CROSS REFERENCE TO RELATED APPLICATIONS

This application is a National Stage of International Application No. PCT/JP2011/069733, filed on Aug. 31, 2011, which claims priority from Japanese Patent Application No. 2010-194068, filed on Aug. 31, 2010, the contents of all of which are incorporated herein by reference in their entirety.

TECHNICAL FIELD

The present invention relates to processes for producing (2R,3R)-2-(2,4-difluorophenyl)-3-(4-methylenepiperidin-1-yl)-1-(1H-1,2,4-triazol-1-yl)butan-2-ol (nonproprietary name (INN): Efinaconazole, hereinafter sometimes abbreviated as KP-103) which is the compound represented by formula 1 and known to be effective against mycotic diseases in humans and animals (the compound described in Example 1 in Patent Document 1) or salts of this compound.

[Formula 1]

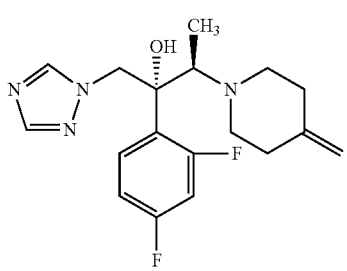

Formula 1

BACKGROUND ART

Methods for obtaining aminoalcohols by the ring-opening addition reaction of epoxides with amines are generally performed at high temperature for a prolonged time using a large excess of amines. Since a large excess of amines are used, the conventional methods give rise to a lot of by-products and require the step of recovering amines; hence, if the amines are expensive, the conventional methods are not desirable not only from the viewpoint of production cost but also as an industrial production process. In order to realize an enhanced reactivity, it has been proposed that the above-described reaction be performed using Lewis acids but the Lewis acids that can be used are either expensive or labile and are not suitable for industrial use; perchlorates or the like are highly toxic and dangerous and because of this low level of safety, they have posed various problems such as the need to take utmost care in use (Non-Patent Documents 1 and 2). It was also reported that by using lithium bromide, the reactivity at room temperature under a solventless condition could be enhanced (Non-Patent Document 3). The method reported in that document uses amines and epoxides that are liquid at ordinary temperature, so its success is probably due to the reaction of the starting materials at high concentrations under a solventless condition. It then follows that this method is not applicable to amines and epoxides that are solid at ordinary temperature, especially those with high melting points.

Returning now to the compound of formula 1, it is produced by the ring-opening addition reaction of an epoxide with an amine as described in Patent Document 1. In this production method, (2R,3S)-2-(2,4-difluorophenyl)-3-methyl-2-[(1H-1,2,4-triazol-1-yl)methyl]oxirane (hereunder sometimes abbreviated as "epoxytriazole") is used as the epoxide and 4-methylenepiperidine (hereunder sometimes abbreviated as "4-MP") is used as the amine. In this method, the ring-opening addition reaction uses a large excess of 4-MP in water and involves prolonged heating under reflux, so it has the disadvantage that a lot of by-products are generated during reaction and need be removed. As a further problem, 4-methylenepiperidine which is produced by the method described in Patent Document 2 is obtained as dissolved in water, so its purity is low enough to affect the reactivity and impurities are unavoidably generated by the heat applied to the step of isolation by distillation.

CITATION LIST

Patent Documents

Patent Document 1: pamphlet of WO94/26734
Patent Document 2: pamphlet of WO97/11939

Non-Patent Documents

Non-Patent Document 1: Synthesis, 2004, No. 10, pp 1563-1565
Non-Patent Document 2: J. Org. Chem., 2007, vol. 72, pp 3713-3722
Non-Patent Document 2: Eur. J. Org. Chem., 2004, No. 17, pp 3597-3600

SUMMARY OF INVENTION

Technical Problem

An object of the present invention is to provide a process for producing the compound of formula 1 in higher yield and with reduced generation of by-products by the ring-opening addition reaction of (2R,3S)-2-(2,4-difluorophenyl)-3-methyl-2-[(1H-1,2,4-triazol-1-yl)methyl]oxirane with 4-methylenepiperidine under mild conditions without using a large excess of 4-methylenepiperidine.

Solution to Problem

As a result of intensive studies, the present inventors found the following: if 4-methylenepiperidine is converted to an acid addition salt of 4-methylenepiperidine, it is free of any possible impurities that may have been included at the stage of acquisition of 4-methylenepiperidine and can be isolated as a highly pure solid, with the consequential result that the purity of 4-methylenepiperidine which is used as a starting material in the ring-opening addition reaction of epoxytriazole with amine can be improved; and if this ring-opening addition reaction of epoxytriazole with amine is performed in a reaction solvent in the presence of a hydroxide of a specific alkali metal or an alkaline earth metal, there is no need to use a large excess of 4-methylenepiperidine and the compound of formula 1 can be produced under mild conditions to give higher yield while reducing the generation of by-products. The present invention has been accomplished on the basis of these findings.

DESCRIPTION OF EMBODIMENTS

The process of the present invention is described below in detail.

The present invention relates to a process for producing the compound of formula (1) which, as formulated below, comprises reacting (2R,3S)-2-(2,4-difluorophenyl)-3-methyl-2-[(1H-1,2,4-triazol-1-yl)methyl]oxirane with an acid addition salt of 4-methylenepiperidine in a reaction solvent in the presence of a hydroxide of an alkali metal or an alkaline earth metal selected from the group consisting of lithium, sodium, calcium, and strontium or a hydrate of the hydroxide:

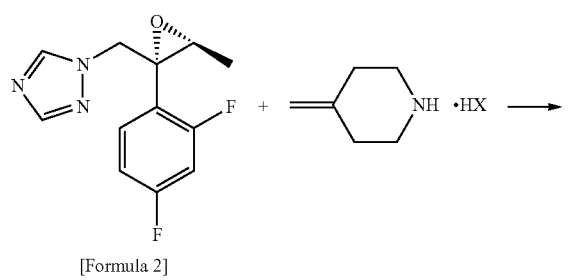

[Formula 2]

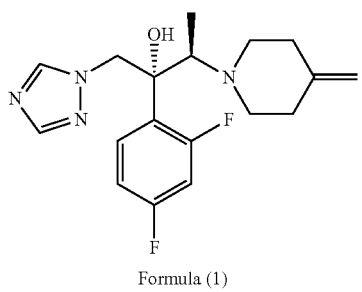

Formula (1)

(where HX signifies the acid in the acid addition salt)

Starting Materials in the Process of the Invention

The process of the present invention can be carried out using the starting compounds in any amounts ranging from the gram level to the ton level, and the amount of the solvent may be determined according to the amounts of the starting compounds to be used.

(2R,3S)-2-(2,4-Difluorophenyl)-3-methyl-2-[(1H-1,2,4-triazol-1-yl)methyl]oxirane can be obtained by the method described in JP 2-191262 A.

The acid addition salt of 4-methylenepiperidine is represented by the following formula:

[formula 3]

In the above formula, HX signifies the acid in the acid addition salt and the acid that forms the acid addition salt of 4-methylenepiperidine may basically be any acid that forms salts with amines and examples include, but are not limited to, inorganic salts such as hydrochloric acid, hydrobromic acid, hydroiodic acid, sulfuric acid, nitric acid, phosphoric acid, boric acid, chloric acid, and carbonic acid, as well as organic acids such as formic acid, acetic acid, trifluoroacetic acid, propionic acid, oxalic acid, methanesulfonic acid, benzenesulfonic acid, and p-toluenesulfonic acid. Preferred examples of the acid include hydrochloric acid, hydrobromic acid, hydroiodic acid, nitric acid, and trifluoroacetic acid, and hydrobromic acid or hydroiodic acid is more preferred.

To obtain the acid addition salt of 4-methylenepiperidine, 4-methylenepiperidine and an acid that corresponds to the acid addition salt may be reacted in the usual manner.

From the viewpoint of production on an industrial scale, 4-methylenepiperidine can preferably be produced by the method described in the pamphlet of WO97/11939. The 4-methylenepiperidine produced by that method is obtained as dissolved in water and contains the impurities that have been generated by the heat applied during isolation by distillation. In contrast, according to the production method described below, the acid addition salt of 4-methylenepiperidine is free of the above-mentioned impurities and can be isolated as a highly pure solid.

Thus, a preferred process for producing the acid addition salt of 4-methylenepiperidine comprises the following two steps:

(1) reacting a solution of 4-methylenepiperidine with an acid that corresponds to the acid addition salt; and
(2) after optionally distilling off the solvent, purifying the resulting product by crystallization or washing in suspension.

Examples of the solution of 4-methylenepiperidine used in step (1) include an aqueous solution, an alcohol solution (e.g. methanol solution), and a solution of a mixed solvent consisting of water and alcohol or the like. The amount to be used of an acid that corresponds to the acid addition salt is preferably from 0.9 to 1.0 equivalent on the basis of 4-methylenepiperidine. The reaction conditions for step (1) are such that it is performed at a temperature ranging from 0° C. to the vicinity of room temperature for a period ranging from 15 minutes to several hours.

After step (1), the solvent may optionally be removed in the usual manner, typically under reduced pressure and either at room temperature or with heating. If the water content of the reaction system is to be reduced, a suitable method may be adopted, such as using a desiccant or azeotropy of a mixture with toluene.

Purification by crystallization or washing in suspension in step (2) may involve either recrystallization after dissolving in a solvent or washing the crystal with a solvent in suspension after it is obtained by distilling off the solvent or by filtration.

Specific conditions for the production method vary with the type of the acid addition salt. In the case of hydrobromide and hydrochloride, the solvent is distilled off after the reaction in step (1) and, thereafter, the resulting crystal is washed with acetone in suspension and filtered off. In the case of p-toluenesulfonate, the solvent is distilled off after the reaction in step (1) and, thereafter, the residue is dissolved in a liquid mixture of ethyl acetate/isopropanol (10:1) and then subjected to recrystallization. In the case of hydroiodide, trifluoroacetate, and nitrate, the solvent is distilled off to dryness after the reaction in step (1) and, then, diisopropyl ether is added to the residue and washing is done in suspension.

Reaction Conditions for the Process of the Invention

The acid addition salt of 4-methylenepiperidine is typically used in amounts ranging from 1 to 5 equivalents, preferably from 1 to 1.5 equivalents, based on epoxytriazole.

Examples of the hydroxide of an alkali metal or an alkaline earth metal to be used in the reaction of the present invention include lithium hydroxide, sodium hydroxide, calcium hydroxide, and strontium hydroxide, as well as hydrates thereof. More preferred are lithium hydroxide, calcium hydroxide, and hydrates thereof, and even more preferred are lithium hydroxide and hydrates thereof.

The amount to be used of the above-mentioned hydroxide of an alkali metal or an alkaline earth metal varies with the type and basicity of the specific compound to be used and it typically ranges from 1 to 5 equivalents, preferably from 1 to 1.5 equivalents, based on the acid addition salt of 4-methylenepiperidine.

Examples of the reaction solvent include: alcohols such as methanol, ethanol, isopropanol, and 1-butanol; aprotic polar solvents (say, esters such as ethyl acetate and butyl acetate; amides such as N,N-dimethylformamide, N,N-dimethylacetamide, and N-methylpyrrolidone; ethers such as tetrahydrofuran, 1,4-dioxane, 1,2-dimethoxyethane, and cyclopentyl methyl ether; other solvents such as acetonitrile, dimethyl sulfoxide, nitromethane, and 4-methyl-2-pentanone); mixtures of two or more of these solvents; and mixed solvents consisting of water and at least one of the above-mentioned solvents. Preferred reaction solvents are acetonitrile, 1,2-dimethoxyethane, cyclopentyl methyl ether, isopropanol, 1-butanol, and 4-methyl-2-pentanone; more preferred are acetonitrile, 1,2-dimethoxyethane, cyclopentyl methyl ether, and isopropanol; even more preferred are acetonitrile and cyclopentyl methyl ether.

The reaction is performed at temperatures in the range from 0° C. to 150° C. with cooling, at room temperature, or with optional heating. The reaction time varies with the reaction temperature, the solvent used, and other factors, but it typically ranges from 1 to 24 hours. The reaction can be performed at any pressure but it is typically performed at ordinary pressure.

The compound obtained by the reaction may be purified in the usual manner as by recrystallization or chromatography.

If desired, the obtained compound of formula 1 may be converted to a salt with an inorganic acid such as hydrochloric acid, sulfuric acid, nitric acid, phosphoric acid or hydrobromic acid, or an organic acid such as fumaric acid, maleic acid, acetic acid, malic acid, tartaric acid, citric acid, methanesulfonic acid or p-toluenesulfonic acid.

On the following pages, the present invention is described more specifically by means of Examples but it should be understood that the present invention is by no means limited by those Examples.

EXAMPLES

Production 1

Production of 4-methylenepiperidine hydrobromide (4-MP.HBr)

4-Methylenepiperidine (4-MP) in a methanol/water mixture at a concentration of 0.8 M was prepared by the method described in the pamphlet of WO97/11939 and 500 mL (0.4 mol) of the solution was cooled with stirring in an ice bath. Thereafter, 61.3 g (0.36 mol) of 48% hydrobromic acid was added in several portions to the cooled solution, which was stirred in an ice bath for an hour. Thereafter, the solvents were distilled off by heating under reduced pressure, whereupon a white crystal precipitated. Subsequently, 50 mL of toluene was added and the solvent was distilled off by heating under reduced pressure to effect azeotropic dehydration; after performing this procedure twice, 192 mL of acetone was added and the mixture was stirred in an ice bath for 2 hours. Thereafter, the crystal was filtered off, washed with 60 mL of acetone (as cooled on an ice bath), dried with air at room temperature, and further dried under reduced pressure at 40° C. for 12 hours to give a colorless crystal of 4-MP.HBr in an amount of 58 g (yield, 90%).

$^1$H-NMR (500 MHz, CDCl$_3$)
δ: 2.62 (4H, t, J=6.09 Hz), 3.26 (4H, t, J=6.09 Hz), 4.90 (2H, s), 9.18 (1H, br).
melting point (DSC): 147-147.9° C.

Production 2

Production of 4-methylenepiperidine p-toluenesulfonate (4-MP.PTSA)

4-Methylenepiperidine (4-MP) as prepared by the method described in the pamphlet of WO97/11939 was subjected to a dehydrating operation and the resulting 4-MP (9.7 g, 0.1 mol) was dissolved in isopropanol (IPA) (50 mL); to the resulting solution, p-toluenesulonic acid monohydrate (PTSA.H$_2$O) (18.1 g, 0.095 mol) in IPA (80 mL) was added and after stirring the mixture at room temperature for 30 minutes (weakly exothermic), IPA was distilled off under reduced pressure and the residue was dissolved in an ethyl acetate/IPA (10:1) mixture (250 mL) with heating. After cooling to room temperature, the solution was left to stand at 0-5° C. for 20 hours and the precipitating crystal was filtered off, washed, and dried to give a white crystal of 4-MP.PTSA in an amount of 23.34 g (yield, 91.2%).

$^1$H-NMR (400 MHz, DMSO-d$_6$)
δ: 2.29 (3H, s), 2.35 (4H, t, J=6.4 Hz), 3.08 (4H, t, J=6.4 Hz), 4.85 (2H, s), 7.13 (2H, d, J=8.2 Hz), 7.49 (2H, d, J=8.2 Hz), 8.58 (2H, br s).

Production 3

Production of 4-methylenepiperidine hydrochloride (4-MP.HCl)

4-Methylenepiperidine (4-MP) as prepared by the method described in the pamphlet of WO97/11939 was subjected to a dehydrating operation and 400 g (4.12 mol) of the resulting 4-MP was cooled with stirring in an ice bath. Thereafter, 350 mL (4.08 mmol) of concentrated hydrochloric acid was added to the cooled solution, which was further stirred in an ice bath. After concentrating under reduced pressure, 300 mL of toluene was added and the mixture was concentrated under reduced pressure to effect azeotropic dehydration; after performing this procedure three times, 300 mL of acetone was added and the mixture was washed in suspension with ice cooling. The crystal was filtered off, washed with acetone, and dried under reduced pressure at room temperature to give 4-methylenepiperidine hydrochloride (4-MP.HCl) in an amount of 336.8 g (yield, 46%).

$^1$H-NMR (500 MHz, CDCl$_3$)
δ: 2.58 (4H, t, J=6.1 Hz), 3.22 (4H, t, J=6.1 Hz), 4.89 (2H, s), 9.70 (1H, br s).

Production 4

Production of 4-methylenepiperidine hydroiodide (4-MP.HI)

4-Methylenepiperidine (4-MP) in a methanol/water mixture at a concentration of 0.66 M was prepared by the method described in the pamphlet of WO97/11939 and 20 mL (13.19 mmol) of the solution was cooled with stirring in an ice bath. Thereafter, 2.66 g (11.84 mmol) of 57% hydroiodic acid was added to the cooled solution, which was stirred in an ice bath for 15 minutes. After concentrating under reduced pressure, 1.6 mL of toluene was added and the mixture was concentrated under reduced pressure to effect azeotropic dehydration; this procedure was performed twice, whereupon a white solid was precipitated. Diisopropyl ether (6 mL) was added and the crystal was washed in suspension at room temperature for an hour. Thereafter, the crystal was filtered off, washed with diisopropyl ether, and dried under reduced pressure at room temperature to give 4-methylenepiperidine hydroiodide (4-MP.HI) in an amount of 2.66 g (yield, 90%).

$^1$H-NMR (500 MHz, CDCl$_3$)

δ: 2.66 (4H, t, J=6.1 Hz), 3.31-3.33 (4H, m), 4.91 (2H, s), 8.34 (1H, br s).

Production 5

Production of 4-methylenepiperidine trifluoroacetate (4-MP.TFA)

Reaction was performed by the same method as described above, except that the 57% hydroiodic acid was replaced by 1.35 g (11.87 mmol) of trifluoroacetic acid (TFA), giving 4-methylenepiperidine trifluoroacetate (4-MP.TFA) in an amount of 2.55 g (yield, 92%).

$^1$H-NMR (500 MHz, CDCl$_3$)

δ: 2.50 (4H, t, J=6.1 Hz), 3.16 (4H, t, J=6.1 Hz), 4.89 (2H, s), 9.52 (1H, br s).

Production 6

Production of 4-methylenepiperidine nitrate (4-MP.HNO$_3$)

Reaction was performed by the same method as described above, except that the 57% hydroiodic acid was replaced by 1.08 g (11.87 mmol) of 69% nitric acid, giving 4-methylenepiperidine nitrate (4-MP.HNO$_3$) in an amount of 1.87 g (yield, 89%).

$^1$H-NMR (500 MHz, CDCl$_3$)

δ: 2.53 (4H, t, J=6.1 Hz), 3.28 (4H, t, J=6.1 Hz), 4.89 (2H, s), 8.85 (1H, br s).

Example 1

Production of (2R,3R)-2-(2,4-difluorophenyl)-3-(4-methylenepiperidin-1-yl)-1-(1H-1,2,4-triazol-1-yl)butan-2-ol (KP-103)

21.26 g (119.4 mmol) of the 4-methylenepiperidine hydrobromide (4-MP.HBr) obtained in Production 1 and 2.859 g (119.4 mmol) of lithium hydroxide were added to 80 mL of acetonitrile and stirred for a while. Thereafter, 20 g (79.6 mmol) of (2R,3S)-2-(2,4-difluorophenyl)-3-methyl-2-[(1H-1,2,4-triazol-1-yl)methyl]oxirane was added and the mixture was heated under reflux in an oil bath (external temperature: 100° C.) for 14 hours. After the reaction completed, ethanol and distilled water were added to the reaction mixture, whereupon a crystal was precipitated. Thereafter, the crystal was filtered off, washed with 40 mL of an ethanol/water mixture, dried with air at room temperature and further dried under reduced pressure at 40° C. for 12 hours to give a pale yellow crystal of KP-103 in an amount of 24.2 g (yield, 87.3%; purity on HPLC, 95.3%).

$^1$H-NMR (500 MHz, CDCl$_3$)

δ: 0.96 (3H, dd, J=2.68, 7.08 Hz), 2.13-2.26 (4H, m), 2.35 (2H, br), 2.70 (2H, br), 2.90-2.94 (1H, q, J=7.08 Hz), 4.64 (2H, s), 4.82 (1H, dd, J=0.73, 14.39 Hz), 4.87 (1H, dd, J=0.73, 14.39 Hz), 5.45 (1H, s), 6.72-6.81 (2H, m), 7.51 (1H, dt, J=6.59, 9.03 Hz), 7.78 (1H, s), 8.02 (1H, s).

FAB-MS m/z: 349 [M+H]$^+$ melting point: 86-89° C.

optical rotation: $[\alpha]_D^{25}$ −87 to −91° (C=1.0, methanol)

Example 2

0.50 g (1.99 mmol) of epoxytriazole, 0.53 g (2.98 mmol) of 4-methylenepiperidine hydrobromide (4-MP.HBr) and 0.07 g (2.96 mmol) of lithium hydroxide were added to 2 mL of acetonitrile and heated under reflux in an oil bath (external temperature, 100° C.) for 14 hours. After distilling off the solvent from the reaction mixture under reduced pressure, water and ethyl acetate were added to the residue and an organic layer was separated. The organic layer was concentrated under reduced pressure and purified by silica gel column chromatography with a hexane/ethyl acetate (1:1) solvent to give KP-103 in an amount of 0.59 g (yield, 86%).

Example 3

Reaction was performed by the same method as in Example 2, except that lithium hydroxide was replaced by 0.22 g (2.97 mmol) of calcium hydroxide, giving KP-103 in an amount of 0.57 g (yield, 82%).

Example 4

Reaction was performed for 19 hours by the same method as in Example 2, except that lithium hydroxide was replaced by 0.36 g (2.98 mmol) of strontium hydroxide, giving KP-103 in an amount of 0.47 g (yield, 68%).

Example 5

0.50 g (1.99 mmol) of epoxytriazole, 0.53 g (2.98 mmol) of 4-methylenepiperidine hydrobromide (4-MP.HBr) and 0.13 g (2.96 mmol) of lithium hydroxide monohydrate were added to 2 mL of acetonitrile and heated under reflux in an oil bath (external temperature, 100° C.) for 14 hours. A sample of the reaction mixture was subjected to HPLC measurement to determine the conversion (relative area percentage of KP-103); KP-103 was verified to have been generated at 81% conversion.

Example 6

Reaction was performed by the same method as in Example 2, except that acetonitrile was replaced by 2 mL of cyclopentyl methyl ether (CPME), giving KP-103 in an amount of 0.63 g (yield, 91%).

Example 7

Reaction was performed by the same method as in Example 2, except that acetonitrile was replaced by 2 mL of 1,2-dimethoxyethane (DME), giving KP-103 in an amount of 0.55 g (yield, 79%).

Example 8

Reaction was performed by the same method as in Example 2, except that acetonitrile was replaced by 2 mL of 1-butanol, giving KP-103 in an amount of 0.59 g (yield, 72%).

Example 9

Reaction was performed by the same method as in Example 2, except that acetonitrile was replaced by 2 mL of isopropanol, giving KP-103 in an amount of 0.50 g (yield, 86%).

Example 10

Reaction was performed by the same method as in Example 2, except that acetonitrile was replaced by 2 mL of 4-methyl-2-pentanone (MIBK), giving KP-103 in an amount of 0.61 g (yield, 88%).

Example 11

Reaction was performed by the same method as in Example 2, except that 4-methylenepiperidine hydrobromide (4-MP.HBr) was replaced by 0.40 g (2.99 mmol) of the 4-methylenepiperidine hydrochloride (4-MP.HCl) obtained in Production 3, whereupon KP-103 was obtained in an amount of 0.47 g (yield, 67%).

Example 12

Reaction was performed by the same method as in Example 2, except that 4-methylenepiperidine hydrobromide (4-MP.HBr) was replaced by 0.67 g (2.99 mmol) of the 4-methylenepiperidine hydroiodide (4-MP.HI) obtained in Production 4, whereupon KP-103 was obtained in an amount of 0.62 g (yield, 90%).

Example 13

Reaction was performed by the same method as in Example 2, except that 4-methylenepiperidine hydrobromide (4-MP.HBr) was replaced by 0.63 g (2.98 mmol) of the 4-methylenepiperidine trifluoroacetate (4-MP.TFA) obtained in Production 5, whereupon KP-103 was obtained in an amount of 0.54 g (yield, 78%).

Example 14

Reaction was performed by the same method as in Example 2, except that 4-methylenepiperidine hydrobromide (4-MP.HBr) was replaced by 0.48 g (3.00 mmol) of the 4-methylenepiperidine nitrate (4-MP.HNO$_3$) obtained in Production 6, whereupon KP-103 was obtained in an amount of 0.49 g (yield, 71%).

Example 15

Reaction was performed for 18 hours by the same method as in Example 2, except that lithium hydroxide was replaced by 0.12 g (2.98 mmol) of sodium hydroxide and 4-methylenepiperidine hydrobromide (4-MP.HBr) was replaced by 0.67 g (2.99 mmol) of the 4-methylenepiperidine hydroiodide (4-MP.HI) obtained in Production 4, whereupon KP-103 was obtained in an amount of 0.51 g (yield, 73%).

INDUSTRIAL APPLICABILITY

The problems posed by the conventional process for producing the compound of formula 1 have been the inclusion of impurities at the stage of acquisition of the starting material 4-methylenepiperidine and the generation of by-products during the production of the compound of formula 1. In contrast, according to the method of the present invention, an acid addition salt of 4-methylenepiperidine is used as a starting material for the production of the compound of formula 1, so it is free from any impurities that may have been included at the stage of obtaining 4-methylenepiperidine and this enables the use of a highly pure solid. In addition, the ring-opening addition of amine to epoxytriazole is promoted in the method of the present invention, so there is no need to use a large excess of 4-methylenepiperidine and the compound of formula 1 can be produced under mild conditions in higher yield while reducing the generation of by-products. Consequently, the method of the present invention enables the compound of formula 1 to be produced on an industrial scale.

The invention claimed is:

1. A process for producing (2R,3R)-2-(2,4-difluorophenyl)-3-(4-methylenepiperidin-1-yl)-1-(1H-1,2,4-triazol-1-yl)butan-2-ol or an acid addition salt thereof, which comprises reacting (2R,3S)-2-(2,4-difluorophenyl)-3-methyl-2-[(1H-1,2,4-triazol-1-yl)methyl]oxirane with an acid addition salt of 4-methylenepiperidine in a reaction solvent in the presence of a hydroxide of an alkali metal or an alkaline earth metal selected from the group consisting of lithium, calcium, and strontium, or a hydrate thereof.

2. The process according to claim 1, wherein the hydroxide of an alkali metal or an alkaline earth metal is lithium hydroxide.

3. The process according to claim 1, wherein the acid addition salt of 4-methylenepiperidine is 4-methylenepiperidine hydrobromide or 4-methylenepiperidine hydroiodide.

4. The process according to claim 3, wherein the acid addition salt of 4-methylenepiperidine is 4-methylenepiperidine hydrobromide.

5. The process according to claim 1, wherein the reaction solvent is acetonitrile, 1,2-dimethoxyethane, cyclopentyl methyl ether, isopropanol, 1-butanol, or 4-methyl-2-pentanone.

6. The process according to claim 5, wherein the reaction solvent is acetonitrile or cyclopentyl methyl ether.

7. A process for producing (2R,3R)-2-(2,4-difluorophenyl)-3-(4-methylenepiperidin-1-yl)-1-(1H-1,2,4-triazol-1-yl)butan-2-ol or an acid addition salt thereof, which comprises reacting (2R,3S)-2-(2,4-difluorophenyl)-3-methyl-2-[(1H-1,2,4-triazol-1-yl)methyl]oxirane with 4-methylenepiperidine hydroiodide in a reaction solvent in the presence of sodium hydroxide.

\* \* \* \* \*